US00PP36418P2

(12) United States Plant Patent
Nakata et al.

(10) Patent No.: US PP36,418 P2
(45) Date of Patent: Feb. 4, 2025

(54) MANDARIN PLANT NAMED 'Mikanken16'

(50) Latin Name: ***Citrus reticulata Blanco* x *Citrus sinensis* (L.) Osbeck**
Varietal Denomination: Mikanken16

(71) Applicant: EHIME PREFECTURE, Ehime (JP)

(72) Inventors: Haruhito Nakata, Ehime (JP); Yukinori Shigematsu, Ehime (JP); Yoji Hyodo, Ehime (JP); Hiroaki Mido, Ehime (JP); Takehiro Kikuchi, Ehime (JP); Yasuyuki Masamoto, Ehime (JP); Takae Sakimoto, Ehime (JP); Hiromichi Yakushiji, Ehime (JP); Takehiro Okusada, Ehime (JP); Taizo Ninomiya, Ehime (JP); Mitsutoshi Okamoto, Ehime (JP); Saki Yamamoto, Ehime (JP); Saki Miyoshi, Ehime (JP); Toya Hioki, Ehime (JP); Kei Kinoshita, Ehime (JP)

(73) Assignee: EHIME PREFECTURE, Matsuyama (JP)

( * ) Notice: Subject to any disclaimer, the term of this patent is extended or adjusted under 35 U.S.C. 154(b) by 0 days.

(21) Appl. No.: 18/658,581

(22) Filed: May 8, 2024

(51) Int. Cl.
*A01H 5/08* (2018.01)
*A01H 6/78* (2018.01)

(52) U.S. Cl.
USPC ..... Plt./202
CPC ..... *A01H 6/785* (2018.05)

(58) Field of Classification Search
USPC ..... Plt./201, 202
CPC ..... A01H 5/0806
See application file for complete search history.

*Primary Examiner* — Kent L Bell
(74) *Attorney, Agent, or Firm* — Seckel IP, PLLC

(57) ABSTRACT

A new variety of *Citrus* 'Mikanken16' that has dark orange fruit color, no seeds, high juiciness, orange-like flavor, ease of peeling the fruit by hand, good appearance and good tasting qualities.

3 Drawing Sheets

Common name: Mandarin.

Botanical classification: *Citrus reticulata* Blanco x *Citrus sinensis* (L.) Osbeck.

Variety denomination: 'Mikanken16'.

BACKGROUND OF THE NEW VARIETY

The present invention relates to a new and distinct variety of Mandarin, *Citrus* L., which has been given the variety denomination 'Mikanken16'.

ORIGIN OF THE VARIETY

The parent varieties are '95-56-25' (male parent) (not patented in the U.S.) and 'Mikanken4' (female parent) (not patented in the U.S.), respectively.

The variety was developed and propagated in Uwajima, Ehime, Japan.

The variety was reproduced asexually by vegetative reproduction by top grafting one-year-old scions on rootstocks, in Uwajima, Ehime, Japan. The name of the rootstock is 'MIYAGAWAWASE' (not patented).

In 2004, crossing the parent varieties and collecting seeds were grown in the next year.

In 2005, 2006 seedlings are grown.

In 2007, they were grafted on top of root stock.

In 2010, the first fruit was harvested and lines were primary selected.

In 2013, plants were secondary selected.

From 2012 to 2022 growing tests for their performance.

In 2023, breeding was completed with DUS status confirmed (distinct, uniform, and stable), whereby it was confirmed that the instant tree reproduces true to type in successive generations of asexual reproduction, and the variety was named 'Mikanken16'.

Cultivation of the variety does not require special conditions or treatments.

The variety is currently mainly intended for fruit production.

SUMMARY OF THE VARIETY

This new mandarin plant 'Mikanken16' has leave blades with no emargination at the tip, fruit with dark orange surface color (JHS color chart No. 1306), medium surface roughness, medium filling of the core, and medium to late maturity for consumption (typically April), that distinguish it notably from its female parent 'Mikanken4'.

Also the fruit of 'Mikanken16' having no collar, no navel opening, and no polyembryony of seeds, as well as having medium surface roughness, medium filling of the core, and medium to late maturity for consumption (typically April), distinguishes it notably from comparative variety 'Shiranuhi' (not patented) and having no navel opening, and no polyembryony of seeds, as well as having dark orange surface color (JHS color chart No. 1306), medium surface roughness, and medium to late maturity for consumption (typically April), distinguishes it notably from comparative variety 'Kiyomi' (not patented).

Specifically, Table 1 below shows a comparison between the instant variety 'Mikanken16' and the female parent 'Mikanken4' as follows (evaluation based on averages):

TABLE 1

Comparison between 'Mikanken16' and 'Mikanken4'

| No. | Characteristics | Female parent 'Mikanken4' States | Present variety 'Mikanken16' States |
|---|---|---|---|
| 36 | Leaf blade: emargination at tip | Present | Absent |
| 99 | Fruit surface: roughness | Smooth | Medium |
| 109 | Fruit: filling of core | Absent or Very Sparse | Medium |
| 127 | Time of maturity of fruit for consumption | Late (May) | Medium to Late (April) |

A comparison with the male parent '95-56-25' is not available because '95-56-25' was an old breeding line, whose states of characteristics are unknown and for which there are no long living plant materials.

Table 2 below shows a comparison between the instant variety 'Mikanken16' and comparative varieties 'Shiranuhi' and 'Kiyomi' as follows (average evaluation):

TABLE 2

Comparison between 'Mikanken16' and 'Shiranuhi' and 'Kiyomi'

| No. | Characteristics | Reference variety 'Shiranuhi' States | Reference variety 'Kiyomi' States | Present variety 'Mikanken16' States |
|---|---|---|---|---|
| 87 | Fruit: presence of collar | Present | | Absent |
| 94 | Fruit: presence of navel opening | Occasionally Present | Occasionally Present | Absent |
| 97 | Fruit surface: predominant color(s) | | Medium Orange (JHS No. 1605) | Dark Orange (JHS No. 1306) |
| 99 | Fruit surface: roughness | Medium to Rough | Smooth to Medium | Medium |
| 109 | Fruit: filling of core | Absent or Very Sparse | | Medium |
| 126 | Seed: polyembryony | Present | | Absent |
| 127 | Time of maturity of fruit for consumption | Medium (March) | Medium (March) | Medium to Late (April) |

BRIEF DESCRIPTION OF THE DRAWINGS

In the accompanying drawings, which are as nearly true as is reasonable possible to make in a color illustration of this type.

Figure 1:
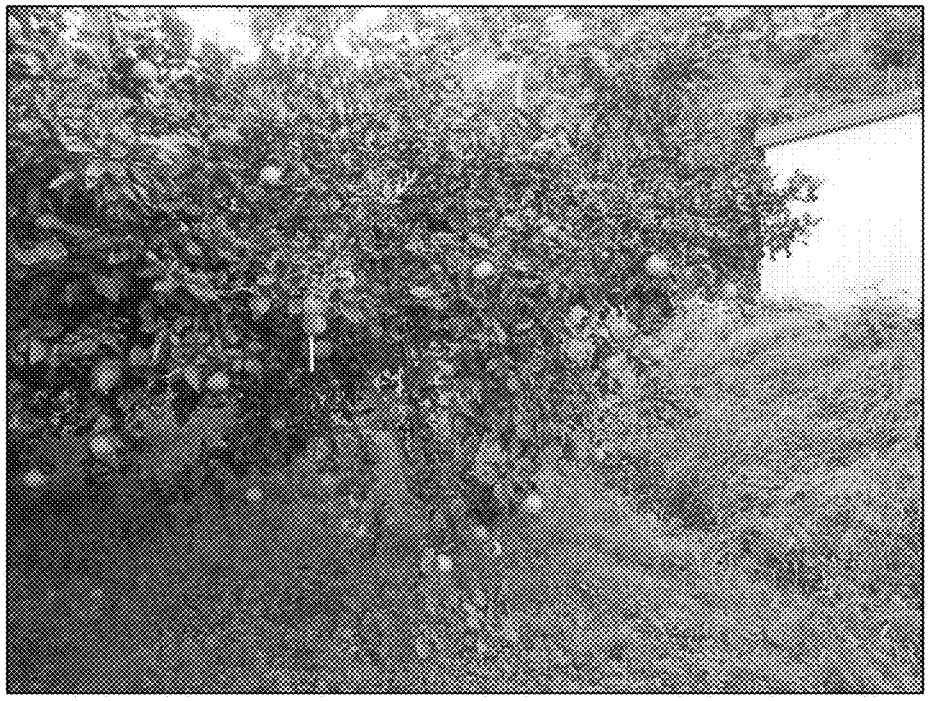
FIG. 1 is a color photograph showing a general view of an illustrative mandarin tree of the variety named 'Mikanken16' bearing fruits.
Figure 2:
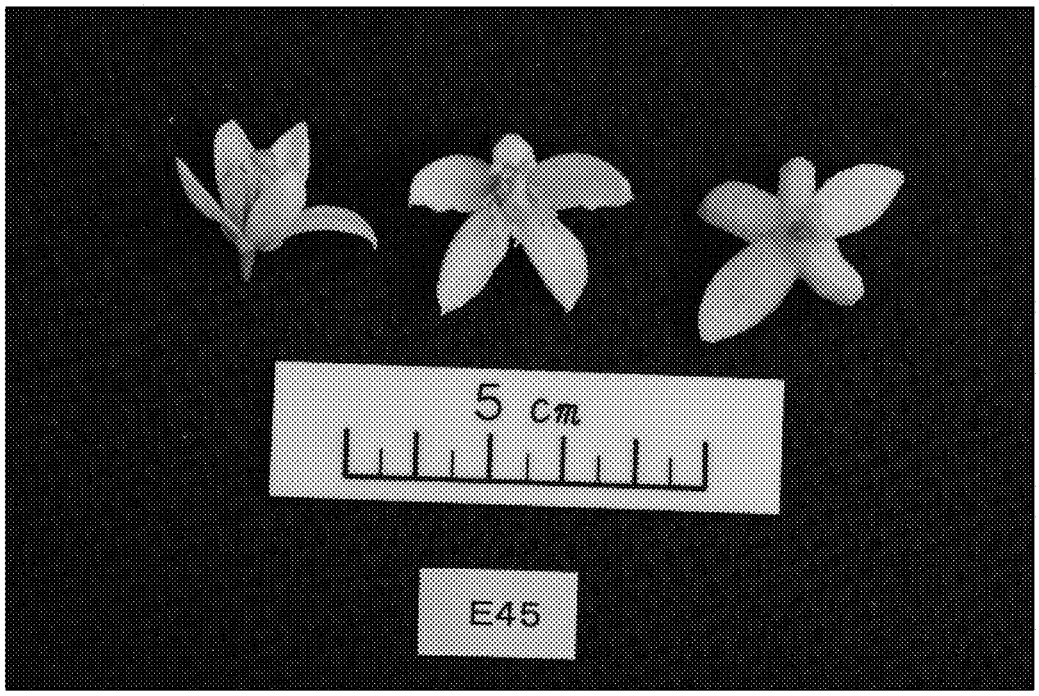
FIG. 2 is a color photograph showing flowers of 'Mikanken16'.
Figure 3:
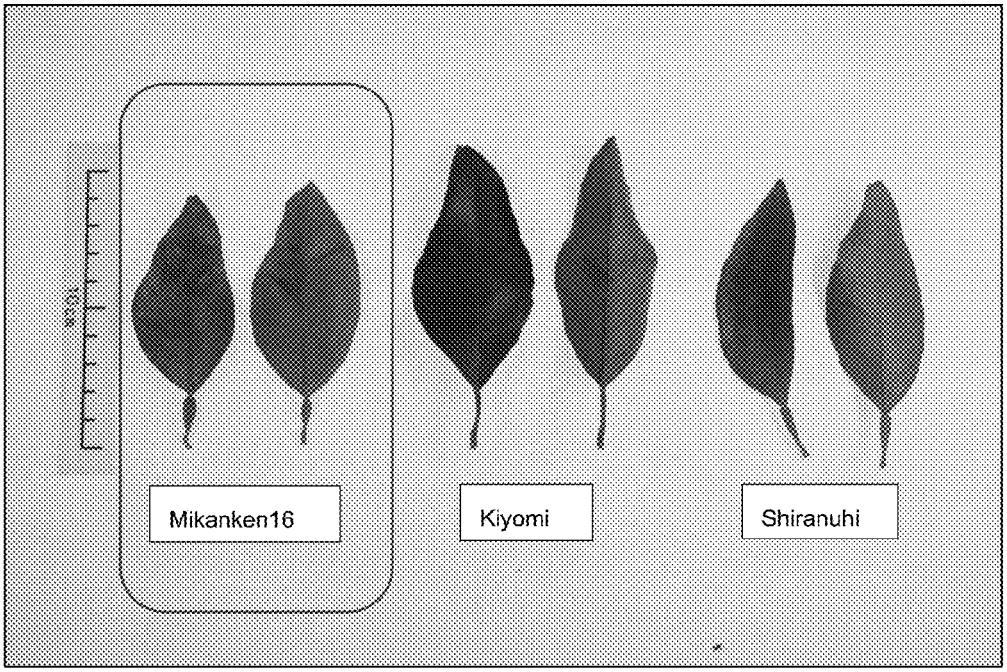
FIG. 3 is a color photograph showing leaves of 'Mikanken16', together with leaves of comparative varieties 'Kiyomi', and 'Shiranuhi'.
Figure 4:
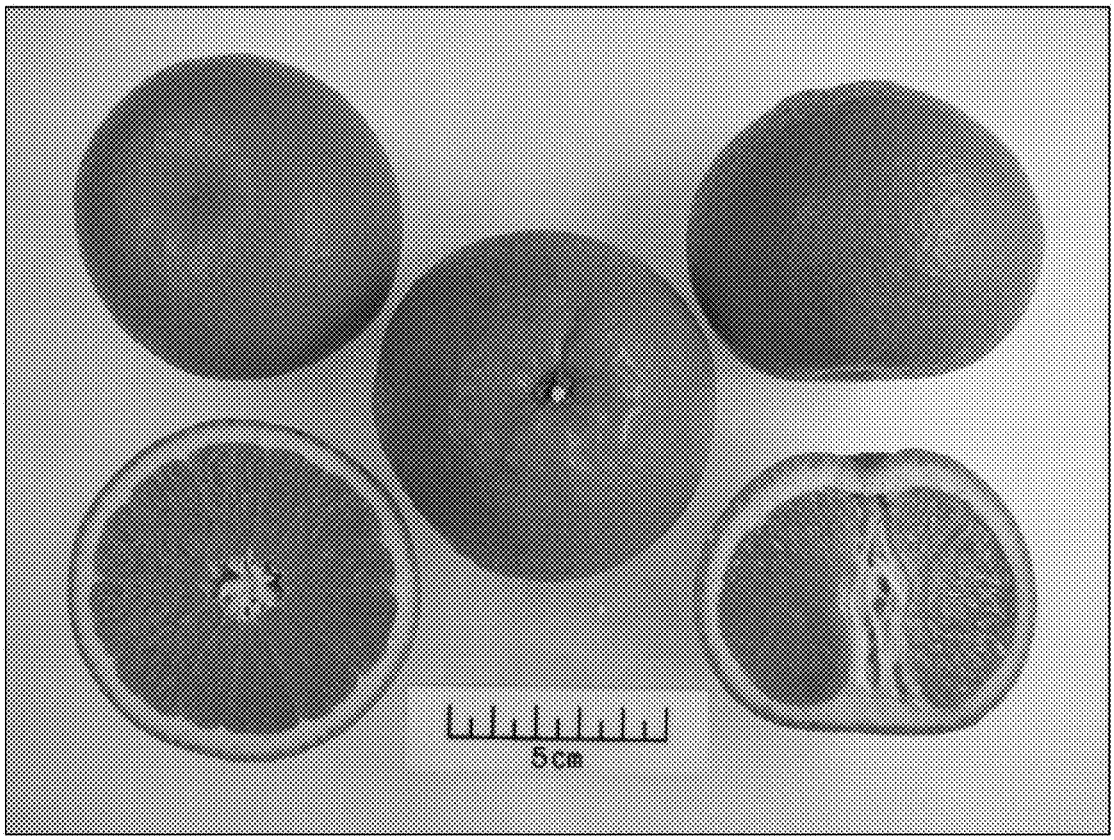
FIG. 4 is a color photograph showing fruits of 'Mikanken16'.
Figure 5:
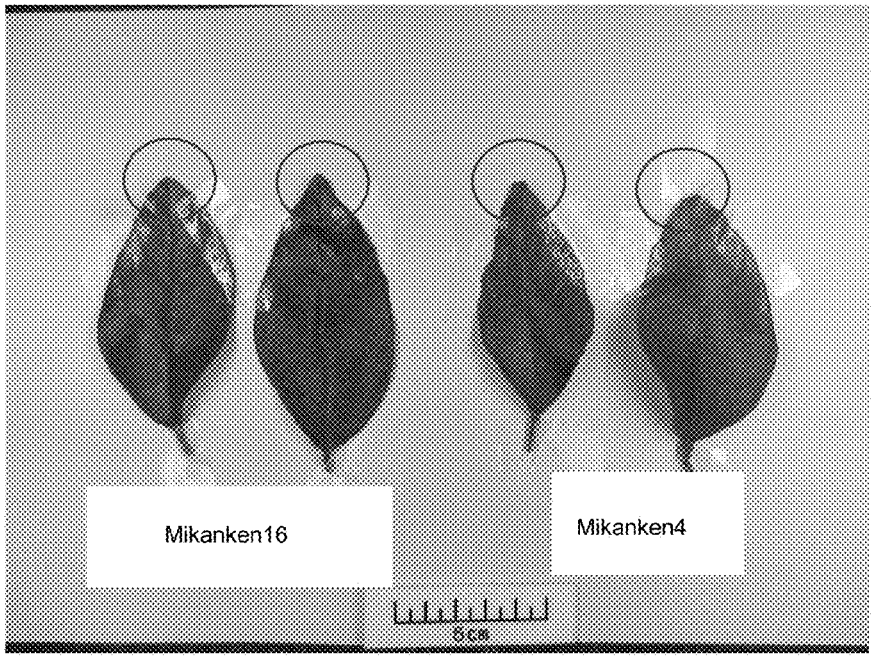
FIG. 5 is a color photograph showing leaves of 'Mikanken16', together with leaves of female parent 'Mikanken4', illustrating the difference between the leaf blades, in that the leave blades of 'Mikanken16' have absent emargination at the tip instead of present emargination at the tip for 'Mikanken4'.
Figure 6:
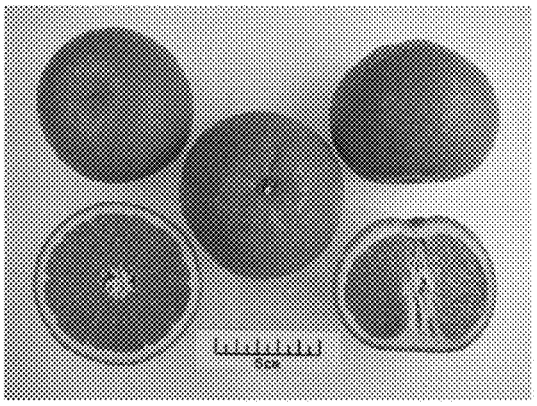
FIG. 6 is a color photograph showing fruits of 'Mikanken16', together with fruits of comparative variety 'Kiyomi', illustrating the difference between the fruit surface predominant colors, in that the fruit surface predominant color of 'Mikanken16' is dark orange (JHS color chart No. 1306) instead of medium orange (JHS color chart No. 1605) for 'Kiyomi', and the difference between the fruit surface roughnesses, in that the fruit surface roughness of 'Mikanken16' is medium instead of smooth to medium for the fruit of 'Kiyomi'.
Figure 6:
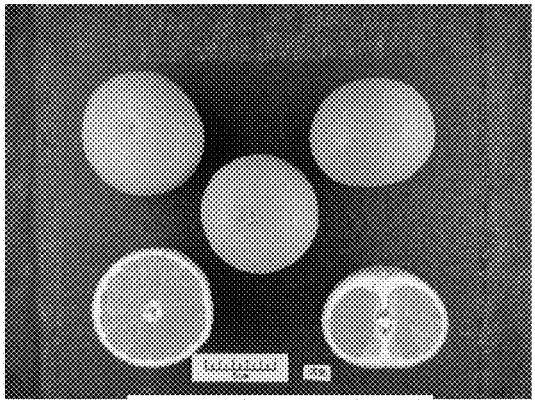
Figure 7:
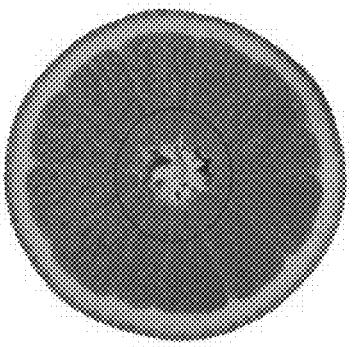
FIG. 7 is a color photograph showing the transverse section of a fruit of 'Mikanken16' together with a fruit of female parent 'Mikanken4', illustrating the difference between the filling of the core, in that the fruit of 'Mikanken16' has medium filling of the core, instead of absent or very sparse filling of the core for the fruit of 'Mikanken4'.
Figure 7:
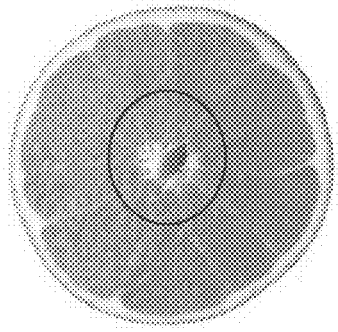

Due to chemical and/or digital development, processing and printing, the plants or portions of plants depicted in the photographs may or may not be precisely accurate, when compared to the actual botanical specimens.

DETAILED DESCRIPTION OF THE INVENTION

Table 3 shows the botanical description of the 'Mikanken16' plants evaluated in 2022 (including the comparison with the reference plants 'KIYOMI' and 'SHIRANUI'). Values as provided are averages. The ages of the trees evaluated was 6 years, and the location of the trees evaluated was in Uwajima, Ehime, Japan.

The 'Mikanken16' plants shown on the photographs were grown at Uwajima, Ehime, Japan. The plants were 3-year grown trees after top grafting. The tree was photographed on Dec. 7, 2016, the flowers were photographed on May 7, 2016, the mature leaves photographed on Jul. 26, 2016 and the fruits were photographed on Mar. 23, 2017.

Colors are given according to the J.H.S. (Japan Horticultural Society) Color Chart.

BOTANICAL DESCRIPTION

TABLE 3

Botanical description of 'Mikanken16'

| No. | Characteristics | States | Values |
|---|---|---|---|
| 1 | Ploidy | Diploid | |
| 2 | Tree: growth habit | Spreading | |
| 3 | Tree's vigor | Strong | |
| 4 | Tree's density of canopy | Medium | |
| 5 | Tree's mature height | | 2.75 m |
| 6 | Tree's mature spread | | 2.95 m |
| 7 | Tree's trunk diameter at a specified height above ground | | 52.3 mm at 10 cm above grafting area |
| 8 | Tree's bark texture | Rough | |
| 9 | Tree's bark color | Green brown | JHS color chart No. 2509 |
| 10 | Branch length | | 12.6 cm |
| 11 | Branch diameter | | 2.8 mm |
| 12 | Branch crotch angle | | 50° |
| 13 | Branch bark texture | Smooth | |
| 14 | Branch bark color | Dark yellow green | JHS color chart No.3508 |
| 15 | Tree: density of spines | Intermediate | |
| 16 | Number of spines | | 2.1 |

TABLE 3-continued

Botanical description of 'Mikanken16'

| No. | Characteristics | States | Values |
|---|---|---|---|
| 17 | Total leaf bearing nodes | | 6.5 |
| 18 | Location of spines | On branches | |
| 19 | Length of spines | | 1.7 mm |
| 20 | Spine diameter | | 0.5 mm |
| 21 | Spine shape | | conical |
| 22 | Spine color | Dark yellow green | JHS color chart No. 3508 |
| 23 | Leaf type | Individual leaf | |
| 24 | Leaf blade: length (apical leaflet in case of compound leaf) | Medium | 7.3 cm |
| 25 | Leaf blade: width (apical leaflet in case of compound leaf) | Medium | 4.3 cm |
| 26 | Leaf blade: ratio length/width (apical leaflet in case of compound leaf) | Very small | 1.7 |
| 27 | Leaf blade: shape in cross section (apical leaflet in case of compound leaf) | Intermediate: curved inwards | |
| 28 | Leaf blade: twisting | Intermediate | |
| 29 | Leaf blade: blistering | Absent or Weak | |
| 30 | Leaf blade: color | Medium green | JHS color chart No.3509 |
| 31 | Leaf or leaflet: color of upper leaf surface | Dark yellow green | JHS color chart No.3509 |
| 32 | Leaf or leaflet: color lower leaf surface | Dark yellow green | JHS color chart No.3507 |
| 33 | Leaf blade: undulation of margin | Absent or Weak | |
| 34 | Leaf blade: incisions of margin | Crenate | |
| 35 | Leaf blade: shape of apex | Acute | |
| 36 | Leaf blade: emargination at tip | Absent | |
| 37 | Single or compound leaves? | Single leaf | |
| 38 | Base descriptor of leaf and/or leaflet | Acute | |
| 39 | Texture of top surface of leaf and/or leaflet | Smooth | |
| 40 | Texture of bottom surface of leaf and/or leaflet | Smooth | |
| 41 | Petiole: length | Medium | 1.9 cm |
| 42 | Petiole diameter | | 1.9 mm |
| 43 | Petiole texture (both surfaces) | | smooth |
| 44 | Petiole color (both surfaces) | Dark yellow green | JHS color chart No.3509 |
| 45 | Petiole: presence of wings | Present | |
| 46 | Petiole wing shape | Vestigial | |
| 47 | Petiole wing length | | 8.0 mm |
| 48 | Petiole wing texture (both surfaces) | Smooth | |
| 49 | Petiole wing color (both surfaces) | Upper and lower: dark yellow green | JHS color chart No. 3508 (upper), 3509 (lower) |
| 50 | Varieties with petiole wings present only: Petiole: width of wings | Narrow | 2.0 mm |
| 51 | Flower: length of petal | Medium | 18.4 mm |
| 52 | Flower: width of petal | Very Broad | 8.3 mm |
| 53 | Flower: ratio length/ width of petal | Small | 2.2 |
| 54 | Flower: length of stamens | — | 10.3 mm |
| 55 | Flower depth | | 2.2 cm |
| 56 | Flower diameter | | 3.5 cm |
| 57 | Petal number per flower | | 5 |
| 58 | Petal shape | Spindle-shaped | |
| 59 | Petal apex | Acute to obtuse | |
| 60 | Petal margin | Slightly curved | |
| 61 | Petal base descriptors | Truncate | |
| 62 | Petal color (both surfaces) | White (both side) | JHS color chart No. 3301 |

TABLE 3-continued

Botanical description of 'Mikanken16'

| No. | Characteristics | States | Values |
|---|---|---|---|
| 63 | Sepal number per flower | | 5 |
| 64 | Sepal shape | Lanceolate | |
| 65 | Sepal apex | Acute | |
| 66 | Sepal color (both surfaces) | Light yellow green (both side) | JHS color chart No. 3304 |
| 67 | Pistil number per flower | | 1 |
| 68 | Stigma color | Light yellow | |
| 69 | Stigma style | Round | |
| 70 | Stigma length | | 0.2 mm |
| 71 | Stigma color | Bright orange yellow | JHS color chart No. 2205 |
| 72 | Anther: color | Medium yellow | JHS color chart No. 2203 |
| 73 | Anther: viable pollen | Low | (>14 ≤ 21%) |
| 74 | Amount of pollen produced | Very few | |
| 75 | Infructescence: clustering of fruits | Present | |
| 76 | Number of fruits per cluster | | 1 |
| 77 | Fruit: length | Long | 7.7 cm |
| 78 | Fruit: diameter | Large | 8.7 cm |
| 79 | Fruit: ratio length/diameter | Medium | 1.13 |
| 80 | Fruit: position of broadest part | At Middle | |
| 81 | Fruit: shape in transverse section | Circular | |
| 82 | Fruit: general shape of proximal part (excluding neck, collar and depression at stalk end) | Flattened | |
| 83 | Fruit: presence of neck | Absent | |
| 84 | Fruit: presence of depression at stalk end | Present | |
| 85 | Fruit: depth of depression at stalk end | Shallow | 2.5 mm |
| 86 | Fruit: presence of constriction at stalk end | Absent | |
| 87 | Fruit: presence of collar | Absent | |
| 88 | Fruit: general shape of distal part (excluding nipple, bulging of navel and depression at distal end) | Flattened | |
| 89 | Fruit: presence of depression at distal end | Present | |
| 90 | Fruit: depth of depression at distal end | Shallow | 1.7 mm |
| 91 | Fruit: presence of areola | Absent | |
| 92 | Fruit: diameter of stylar scar | Very small | 1.4 mm |
| 93 | Fruit: persistence of style | None | |
| 94 | Fruit: presence of navel opening | Absent | |
| 95 | Fruit: presence of radial grooves at distal end | Absent | |
| 96 | Fruit: expression of radial grooves at distal end | Absent or Very Weak | |
| 97 | Fruit surface: predominant color(s) | Dark orange | JHS color chart No. 1306 |
| 98 | Fruit surface: glossiness | Medium | |
| 99 | Fruit surface: roughness | Medium | |
| 100 | Fruit surface: diameter of oil glands | All about the same diameter | 1.5 mm |
| 101 | Fruit rind: adherence to flesh | Weak | |
| 102 | Fruit rind: strength | Weak | |
| 103 | Fruit rind: conspicuousness of oil glands on inner surface | Absent or Weakly Conspicuous | |
| 104 | Fruit rind thickness | | 3.5 mm |
| 105 | Fruit rind ease of peeling | Somewhat easy | |
| 106 | Fruit: color of albedo | Light yellow | JHS color chart No. 1905 |
| 107 | Fruit: density of albedo | Medium | |
| 108 | Fruit: main color of flesh | Dark orange | JHS color chart No. 1306 |
| 109 | Fruit: filling of core | Medium | |
| 110 | Fruit: presence of rudimentary segments | Absent or Very Weak | |
| 111 | Number of segments per fruit | | 12 |

TABLE 3-continued

| Botanical description of 'Mikanken16' | | | |
|---|---|---|---|
| No. | Characteristics | States | Values |
| 112 | Fruit: strength of segment walls | Medium | |
| 113 | Fruit; conspicuousness of juice vesicle walls | Medium | |
| 114 | Fruit: presence of navel (viewed internally) | Absent or Very Rare | |
| 115 | Fruit: juiciness | High | |
| 116 | Fruit juice: total soluble solids | High | 13.1 Brix |
| 117 | Fruit juice: acidity | Medium | 1.02 |
| 118 | Juice sac length | | 8.4 mm |
| 119 | Juice sac width | | 2.8 mm |
| 120 | Juice color | Dark orange | JHS color chart No. 1306 |
| 121 | Fruit: strength of fiber | Medium | |
| 122 | Fruit: number of seeds (controlled manual self-pollination) | Absent or Very Few | 0 |
| 123 | Fruit: number of seeds (open pollination) | Absent or Very Few | 0 |
| 124 | Fruit weight | | 233.21 g |

TABLE 3-continued

| Botanical description of 'Mikanken16' | | | |
|---|---|---|---|
| No. | Characteristics | States | Values |
| 125 | Fruit productivity: amount of fruit produced per tree per season | | 35 kg/tree |
| 126 | Seed: polyembryony | Absent | |
| 127 | Time of maturity of fruit for consumption | Medium to Late | April |
| 128 | Fruit: parthenocarpy | Present | |
| 129 | Plant: self-incompatibility | Present | |

Other features of the plant are as follows:

Disease and pest resistance: Normal resistance was observed for pests and diseases in Uwajima, Ehime, Japan.

Tree hardiness: USDA Hardiness Zone 9a-9b (until −3° C.).

Fruit shipability: Medium.

Fruit storageability: Medium.

The invention claimed is:

1. A new and distinct variety of *Citrus* plant named 'Mikanken16', substantially as described and illustrated herein.

* * * * *

Mikanken16

Kiyomi

Mikanken16

Mikanken 4